(12) United States Patent
Nielsen et al.

(10) Patent No.: US 8,657,801 B2
(45) Date of Patent: Feb. 25, 2014

(54) SWITCHING DEVICE AND AN IRRIGATION SYSTEM COMPRISING THE DEVICE (75) Inventors: Jakob Ilskov Nielsen, Valby (DK); Jens Peter Bredholt, Klampenborg (DK); Alister David Morton, Kastrup (DK); Klaus Sommer Ipsen, Vanløse (DK); Henrik Jeppesen, Holte (DK)

(73) Assignee: Coloplast A/S, Humlebaek (DK)

( * ) Notice: Subject to any disclaimer, the term of this patent is extended or adjusted under 35 U.S.C. 154(b) by 361 days.

(21) Appl. No.: 12/530,625

(22) PCT Filed: Mar. 14, 2008

(86) PCT No.: PCT/EP2008/053116
§ 371 (c)(1),
(2), (4) Date: Sep. 10, 2009

(87) PCT Pub. No.: WO2008/110629
PCT Pub. Date: Sep. 18, 2008

(65) Prior Publication Data
US 2010/0087792 A1     Apr. 8, 2010

Related U.S. Application Data (60) Provisional application No. 60/906,831, filed on Mar. 14, 2007.

(30) Foreign Application Priority Data

Mar. 14, 2007  (DK) .................................. 2007 00391

(51) Int. Cl.
*A61F 5/44*     (2006.01)

(52) U.S. Cl.
USPC ................. 604/328; 604/29; 604/32; 604/33; 604/34; 604/80; 604/246; 604/247; 604/248; 604/258; 604/410; 251/4; 251/6; 251/9; 137/625.41; 137/861; 137/862; 137/872; 137/874

(58) Field of Classification Search
USPC .................................. 604/248, 258, 328, 410
See application file for complete search history.

(56) References Cited

U.S. PATENT DOCUMENTS

| 4,821,996 A | 4/1989 | Bellotti et al. |
| 5,113,906 A * | 5/1992 | Hogner ......................... 137/595 |
| 6,589,197 B1 * | 7/2003 | Doi et al. ....................... 604/6.1 |

FOREIGN PATENT DOCUMENTS

WO    WO 2004/006993    *  1/2004

\* cited by examiner

*Primary Examiner* — Tatyana Zalukaeva
*Assistant Examiner* — Ilya Treyger
(74) *Attorney, Agent, or Firm* — Coloplast Corp., Coloplast A/S; Nick Baumann (57) ABSTRACT

The invention provides a switching device for an irrigation system. The switching device provides selective communication between a supply port to which a supply of fluid under pressure can be attached and a balloon port to which a fixing balloon of a catheter can be attached, and between the supply port and a port to which a liquid reservoir can be attached. By use of a selection handle, the user can deform conduits in a pre-determined sequence and thus control an irrigation procedure by opening and closing fluid flow in various conduits. The invention further provides an irrigation device incorporating the switching device and a method of controlling a fluid flow e.g. in an irrigation system.

10 Claims, 7 Drawing Sheets

SWITCHING DEVICE AND AN IRRIGATION SYSTEM COMPRISING THE DEVICE

CROSS-REFERENCE TO RELATED APPLICATIONS

This application is a national stage entry of PCT/EP08/53116 filed on Mar. 14, 2008, which was filed with a claim to the benefit of the filing date of U.S. provisional application serial No. 60/906,831 filed on Mar. 14, 2007 and foreign Danish patent application PA 2007 00391 filed on Mar. 14, 2007.

CLAIM OF BENEFIT TO EARLIER-FILED APPLICATIONS

This application is U.S. application Ser. No. 12/530,625, filed Sep. 10, 2009 published as U.S. Pat. Appl. No 2010/0087792 on Apr. 8, 2010, and is the US national phase application of PCT application PCT/EP2008/053116 filed on Mar. 14, 2008 designating the United States and published in English as WO2008/110629 on Sep. 18, 2008, which claimed the priority of Danish App. Ser. No, 2007/00391, filed on Mar. 14, 2007 and of U.S. Prov. App. Ser. No. 60/906,831, filed Mar. 14, 2007, now abandoned. Priority to each of the foregoing is claimed.

INTRODUCTION

The invention generally relates to fluid control and in particular to a switching device for an irrigation system of the kind which comprises a reservoir containing a liquid, a supply of a fluid under pressure, and a catheter provided with a balloon for fixing the catheter in a body cavity. The switching device comprises a balloon conduit, a reservoir conduit, a delivery conduit, and a handle to control a flow in the conduits in accordance with an irrigation sequence.

BACKGROUND OF THE INVENTION

Irrigation systems are used e.g. by people suffering from spinal cord injuries, spina bifida or multiple sclerosis. For such users, irrigation may improve quality of life by preventing constipation, reducing time spent for bowel emptying procedures, reducing fecal incontinence, and by increasing independency in general.

Various irrigation systems are known in the art. A widely used system comprises a catheter configured and sized to be inserted into the patient's rectum where it is maintained in a fixed position by an inflatable balloon. The system comprises a manual pump, typically a balloon pump, which is in fluid communication with the balloon via a balloon conduit. The fluid flow in the balloon conduit can be controlled via a balloon valve. A delivery conduit is secured between a reservoir which contains a liquid, e.g. lavage liquid, and an inlet of the catheter. A manual pump, typically the aforementioned balloon pump, is in fluid communication via a reservoir conduit with the reservoir. By use of the pump, the user can pump regular air or gas into the reservoir and thereby displace the liquid out of the reservoir and into the delivery conduit and via the catheter into the patient. A reservoir valve is operable to control the fluid flow in the reservoir conduit, and a delivery valve is operable to control liquid flow in the delivery conduit.

Sometimes, the balloon is inflated by use of air, and sometimes the balloon is inflated by use of the liquid. If the same pump is used both for inflating the balloon and for displacing the liquid out of the reservoir, all three valves must be operated sequentially with a precise timing. In known systems, flow in the conduits is typically controlled by use of traditional valves such as cylinder valves or ball valves etc. Such valves are relatively expensive, they are relatively heavy, and they typically require much space.

DESCRIPTION OF THE INVENTION

It is an object of embodiments of the present invention to improve fluid control in connection with irrigation systems and irrigation procedures. It is a further object to provide a simple and reliable fluid switch which facilitates a hygienic and safe irrigation. Accordingly, the invention, in a first aspect, provides a switching device of the kind mentioned in the introduction and further comprising a selection handle comprising a pinch cam-surface with a surface pattern arranged to control deformation of the conduits to vary a flow resistance in the conduits in accordance with an irrigation sequence during movement of the handle relative to the conduits.

Since flow in the conduits is controlled by deformation of the conduits, very simple valves can be obtained at very low costs, weight and dimensions, and due to the pinch cam-surface, the deformation can be performed, e.g. by pinching, in a sequence without requiring difficult operation of different valves individually.

The conduits could typically be soft medical hoses made from silicone or from another similar material with shape memory so that a hose returns to its original shape when a pinching pressure is stopped. Liquid carrying conduits could be larger than conduits carrying gas. For conduits carrying gas, a cross-sectional dimension of the flow path in the size of 2.5 mm and a wall thickness in the size of 1 mm could be selected, and for conduits carrying a liquid, a cross-sectional dimension of the flow path in the size of 5.0 mm and a wall thickness in the size of 1 mm could be selected. Several conduits can be provided as a multilumen hose in which two or all three conduits are formed in one piece.

The pinch cam-surface could be a surface with any kind of surface pattern or contour by which the surface may interact with the conduits to change a shape of the conduits and thereby to change flow resistance in the conduits. As an example, the cam surface may pinch a conduit which in an un-pinched state forms an open flow path. In another example, the conduit can be biased towards a collapsed and thus closed state by a spring or by similar means capable of applying a pressure to the outer surface of the conduits, and this pressure can be released by the pinch cam-surface. In yet another example, the conduits are constituted by hoses having, in a relaxed state, a collapsed and thus closed shape which, by deformation, can be brought to an open state. In the following description, the interaction between the pinch cam-surface and the conduits is described as "pinching". However, any kind of interaction between the pinch cam-surface and the conduits either to open or to close the conduits may constitute feasible alternatives.

In one embodiment, the balloon conduit extends between a first port and a second port, the reservoir conduit extends between a third port and a fourth port, and the delivery conduit extends between a fifth port and a sixth port. The fluid in question could be a gas, e.g. regular atmospheric air, or a liquid, e.g. water. If the same fluid under pressure is used both to inflate the balloon and to displace liquid out of the reservoir, the first port and the sixth port could be joined into one port forming an air-inlet, and the device may comprise a pump in direct contact therewith, e.g. a balloon hand pump.

The conduits may be located between a counter body and the pinch cam-surface so that the pinching occurs by direct contact between the conduit and the pinch cam-surface. The counter body, the pinch cam-surface, and the selection handle could be made of plastic, and in particular the pinch cam-surface could be made of a material with a very low surface friction, preferably a friction which is lower than the corresponding surface friction of a grippable portion of the selection handle, by which portion the user can move the pinch cam-surface.

Since it is important in connection with irrigation to ensure swift and complete opening and closing of the passages through the conduits, it may be desired to arrange between the conduits and the pinch cam-surface, pinch elements being moved by the pinch cam-surface, preferably in a direction perpendicular to the conduits, to deform the conduits and thereby provide a complete closing of the conduits when pressed to the closed configuration. The pinch elements may e.g. comprise a relatively sharp, or at least pointed, end which faces towards the conduits.

By movement of the selection handle in one direction, the switching sequence may comprise at least two states:

In a first state the balloon conduit is open so that the fluid under pressure is supplied for inflating the balloon and thereby for fixing the catheter in the body cavity. In this state, the reservoir conduit and delivery conduit are closed to prevent introduction of liquid into the body of the patient before the catheter is fixed.

In a second state, the catheter is fixed in the body and the balloon conduit is closed to prevent further inflation of the balloon. In the second state, the reservoir conduit and the delivery conduit are open so that the fluid under pressure is used for displacing the fluid out of the reservoir and into the body of the patient.

A third state may further be provided in which the balloon conduit and the reservoir conduit are vented, i.e. they are both open to ambient space to deflate the balloon and the reservoir. This is desired when the irrigation procedure is ended. In the third state, the delivery conduit is preferably closed to prevent liquids to enter the catheter or the body when the balloon is not properly inflated. In the third state, the balloon and reservoir conduits could be vented by use of a release valve which opens a passage between the conduits and an ambient space. In addition to the opening of the conduits, the selection handle may further comprise a cam surface which activates the release valve.

As it appears, the delivery conduit is preferably open only in one single state, namely during flushing of the liquid into the body of the patient. It is desirable to allow an endless loop wherein the sequence is repeated for repeated movement of the selection handle in one direction and where the third state is followed directly by the first state without re-entering the second state. For this purpose, and to provide a good user interface, it is desired to provide the device so that the switching sequence is triggered by rotation of the selection handle. Accordingly, the selection handle could be rotatable around a centre-point, and the pinch cam-surface could be formed circularly or at least semi-circularly around the centre-point. In this way, it is achieved that the balloon conduit may change from the venting state to the inflating first state without entering into the second state in which liquids may be spilled out through the catheter.

When moving from the third state to the first state and further to the second state, the reservoir conduit switches from an open state to a closed state and back to an open state and the balloon conduit switches from an open state to a closed state. In the same sequence, the delivery conduit merely switches from a closed state to an open state.

To achieve this sequence by use of one single rotational selection handle, the selection handle may comprise a first and a second displaced pinch cam-surface. E.g. pinch cam-surfaces which are ring-shaped and radially displaced to rotate around the centre-point at different radial distances from the centre-point, and the pinch elements are correspondingly radially displaced from the centre-point to ensure that the pinch cam-surfaces move different pinch elements during rotation of the selection handle. In other words, the sequence may comprise a sub-sequence in which one of the first and second pinch cam-surfaces maintains one of the conduits in one state, e.g. an open, un-pinched, state while the other one of the first and second pinch cam-surfaces switches the state of another conduit between an open state and a closed state.

In an optional fourth state, all conduits are open. Since constant pinching of a conduit for a longer period of time may influence the structure of the conduit and in worst case prevent complete return to an un-pinched shape, the fourth state promotes storage of the device for a longer period of time.

The release valve could be operated via a release cam-surface which also forms part of, or is connected to the selection handle. In one embodiment, the pinch cam-surfaces which controls the flow in the conduits are formed in a lower surface of disc or plate-shaped element, e.g. as two ring shaped elevated surface portions with different radial distance from a centre-point around which the plate-shaped element is adapted to rotate. An opposite, upper, surface of the plate-shaped element forms the grippable portion of the selection handle, or forms an interface to a separate grippable portion which is attached to the plate-shaped element e.g. adhesively, by friction, or by use of screws, rivets etc. In this embodiment, the release cam-surface could be formed as an additional surface portion on the lower surface or the release cam-surface could form part of an edge of the plate-shaped element, i.e. between the lower surface and the upper surface. In this case, the release cam-surface forms a protrusion which extends radially outward away from the centre-point.

Since the fluid under pressure which is used for inflating the balloon could be the same fluid which is used for displacing the liquid out of the reservoir, the first and third port could be one joined port, e.g. with a joined connection arrangement for connection of the switching device to a source of the fluid under pressure. In one embodiment, the first and third port is directly joined with a hand pump, e.g. a balloon pump which thereby forms part of the switching device.

Since the balloon could also be inflated by the liquid which is contained in the reservoir, the first port and the fifth port could also be joined ports, or they may both be in fluid connection with the reservoir so that both the balloon conduit and the delivery conduit conducts liquid from the reservoir to the balloon and to the catheter inlet respectively.

By use of the present invention, anal irrigation can be carried out by the following steps:

The reservoir is filled with a liquid, e.g. regular tap water,

The reservoir and the catheter is connected to the switching device, and if the switching device does not have an integrated pump for providing the fluid under pressure, a source of fluid under pressure is attached.

The selection handle is positioned in accordance with the second state and the liquid is displaced out of the bag until the catheter is filled with the liquid.

The catheter is positioned, and the selection handle is positioned in accordance with the first state and the balloon is inflated to fix the catheter in the body.

The selection handle is positioned in accordance with the second state and irrigation is conducted.

The selection handle is positioned in the venting state, and the catheter is removed.

The pinch structure may comprise, for each conduit, a base portion, e.g. a portion which forms part of the afore-mentioned counter body, which are fixed relative to the conduits, and pinch elements movable relative to the base portions. The base portion and corresponding pinch element are arranged on opposite sides of the conduit so that the conduit is pinched between them. In this embodiment, the base portions may form linear guiding bearings for the pinch elements, e.g. by forming the base portions with cylindrical upwardly extending element so that the pinch element can be slidingly received within cylindrical sidewalls thereof.

The sidewalls could comprise slits through which the conduits may extend. In that way, the conduits are held in a fixed position relative to the pinch structure, and displacement of the conduits during pinching is avoided. As a further advantage, the conduits may rest against two points of the sidewall of the base portion, and the pinch element may press against the conduit at a location between the two wall parts. This improves the ability to close the conduits completely, e.g. by kinking the conduits between the three points.

When a downward pressure of a pinch cam-surface onto a pinch element is discontinued, the corresponding conduit should switch from a closed state to an open state. This can be facilitated partly by use of silicone or similar material with a memory characteristics for the conduits and partly by incorporating a spring effect which bias the pinch elements away from the conduits towards the corresponding pinch cam-surface. The spring effect can be provided by use of individual springs arranged in connection with each pinch element. To facilitate an easy assembly of the device, the pinch elements may, however, form part of a single component, and this component could be shaped so that a desired spring force or spring characteristics is obtained therefrom.

In a second aspect, the invention provides an irrigation system comprising a first connector for connecting a reservoir with liquid, a second connector for connecting a supply of a fluid under pressure, a catheter provided with a balloon for fixing the catheter in a body cavity, and a switching device of the kind described above.

The fluid under pressure can be supplied by a hand pump which may be formed integrally with the switching device so that the second connector forms a fixed connection with the hand pump. In a similar manner, the reservoir may be a plastic bag or a similar relatively simple container structure which may be formed in one part with the switching device so that the first connector forms a fixed connection with the reservoir.

The fluid could be regular air, an alternative gas, or it could be a liquid, e.g. the liquid contained in the reservoir.

In a third aspect, the invention provides a method of controlling a fluid flow in an irrigation system, the irrigation system comprising a reservoir containing a liquid, a supply of a fluid under pressure, a catheter provided with a balloon for fixing the catheter in a body cavity, and a distribution set with a balloon conduit between a first port and a second port, a delivery conduit between a third port and a fourth port, and a delivery conduit between a fifth port and a sixth port. The method comprises that the conduits are pinched to select between flow of the fluid to one of the balloon and the reservoir. In particular, the conduits are pinched by movement of a pinch cam-surface over a pinching element which thereby deforms a conduit.

In a fourth aspect, the invention provides for general use, a switching device comprising:

a distribution set comprising conduits forming flow paths between ports, the conduits being deformable by an outer pressure to vary a flow resistance in the conduits, a pinch structure comprising for each conduit, a pinch element being movable to provide an outer pressure deforming the conduits, and a selection handle rotatable relative to the pinch structure and comprising a first and a second displaced pinch cam-surfaces, the surfaces being arranged to move different pinch elements during rotation of the selection handle.

Any one of the second, third and fourth aspects of the invention may be combined with any of the features mentioned in connection with the first aspect of the invention.

DETAILED DESCRIPTION OF PREFERRED EMBODIMENTS

Preferred embodiments of the invention will now be described in further details with reference to the drawing in which.

Figure 1:
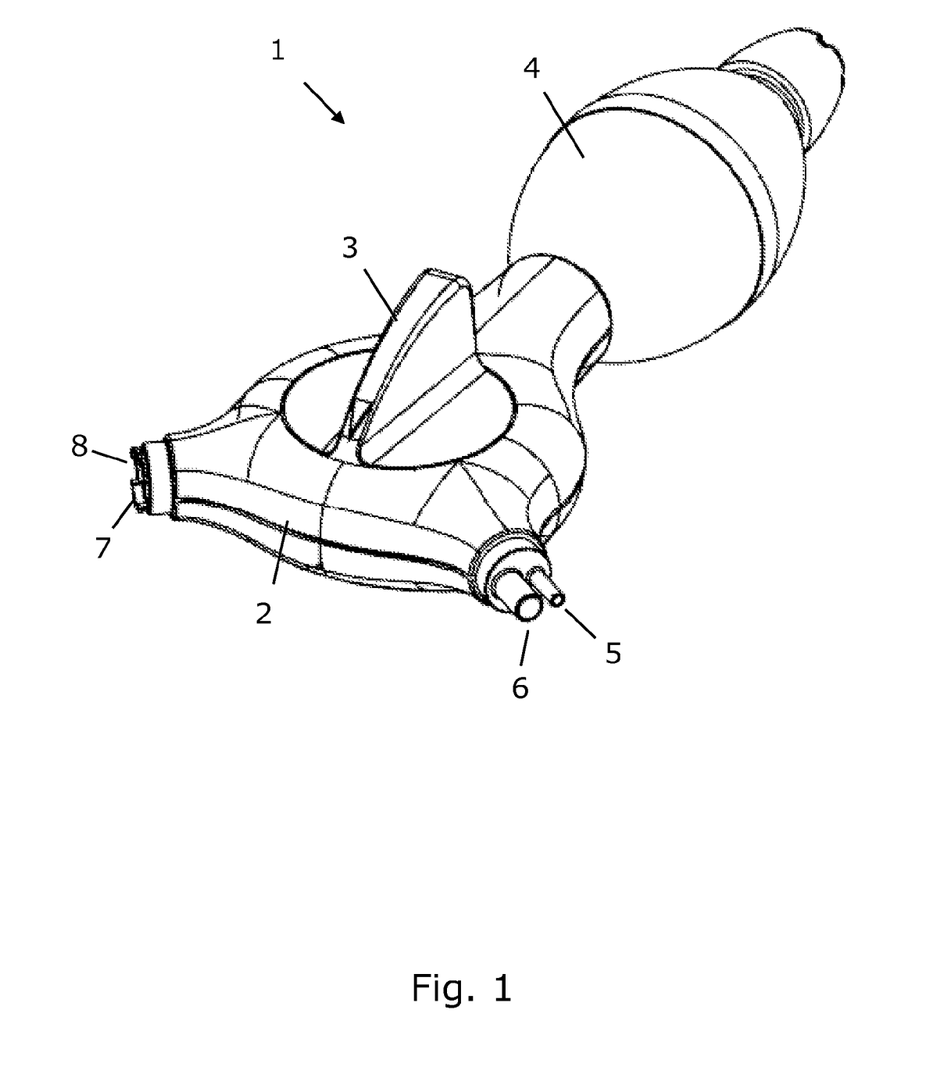
FIG. 1 illustrates a switching device in a perspective view.

As shown in FIG. 1, a switching device 1 in accordance with the invention comprises a housing 2 and a grippable portion 3 of a selection handle, a balloon pump 4 provides a fluid under pressure, namely regular air under pressure, and a number of ports 5, 6, 7, 8 are available for connection of a reservoir and a catheter.

Figure 2:
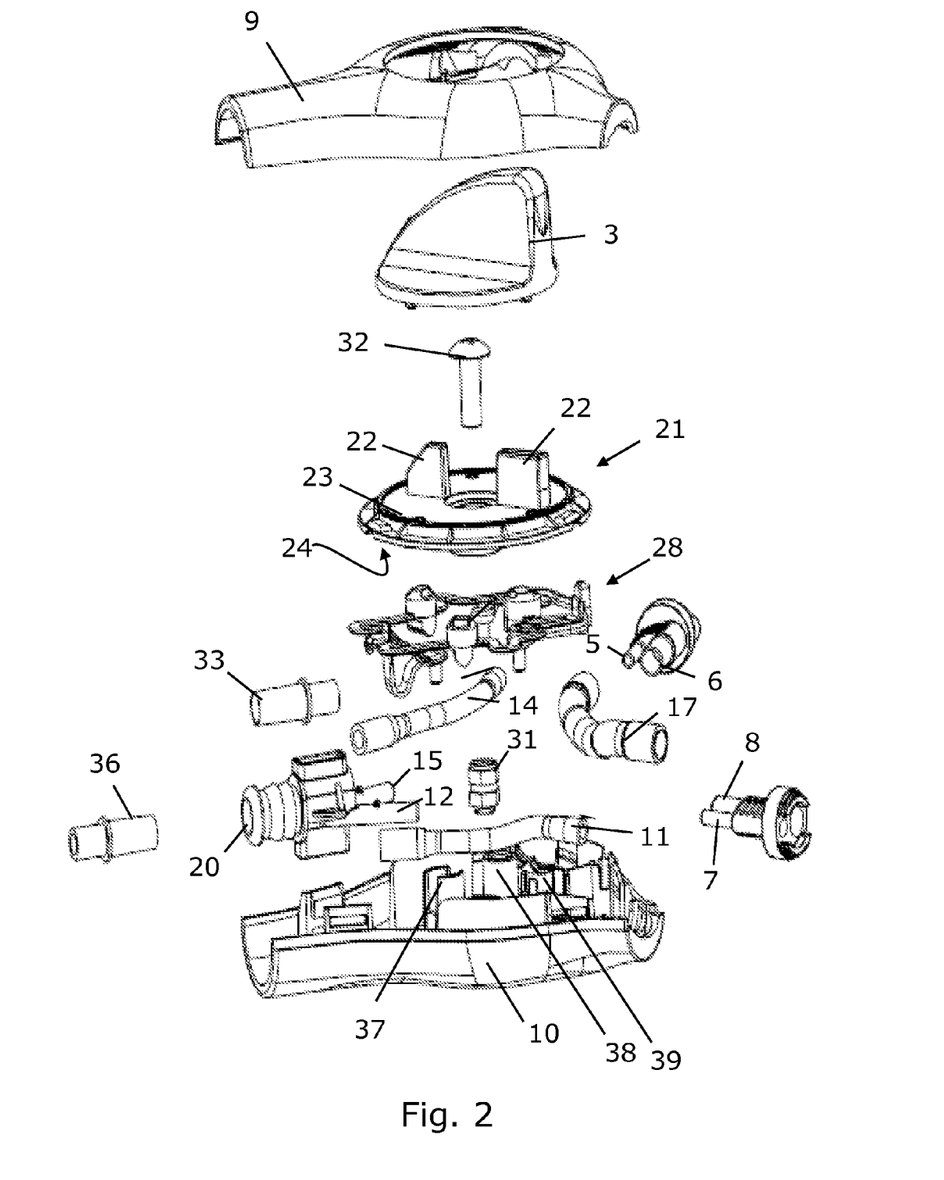
FIG. 2 illustrates the switching device in an exploded view.

FIG. 2 illustrates further details of the device in FIG. 1. The device comprises an upper housing shell 9, a lower housing shell 10 made of injection molded plastic. Internally, between the shells, the device comprises a distribution set with a balloon conduit 11 extending between a first port 12 and a second port 7. The distribution set further comprises a reservoir conduit 14 extending between a third port 15 and a fourth port 5. The distribution set further comprises a delivery conduit 17 extending between a fifth port 6 and a sixth port 8. The first port 12 and the third port 15 are joined into one single conduit in the connector 20 to which a balloon pump 4 (c.f. FIG. 1) can be connected. The second port 7 and the sixth port 8 are formed in one single component, but the corresponding conduits are not joined. The fourth port 5 and the fifth port 6 are also formed in one singe component, again without merging the corresponding conduits.

Figure 3:
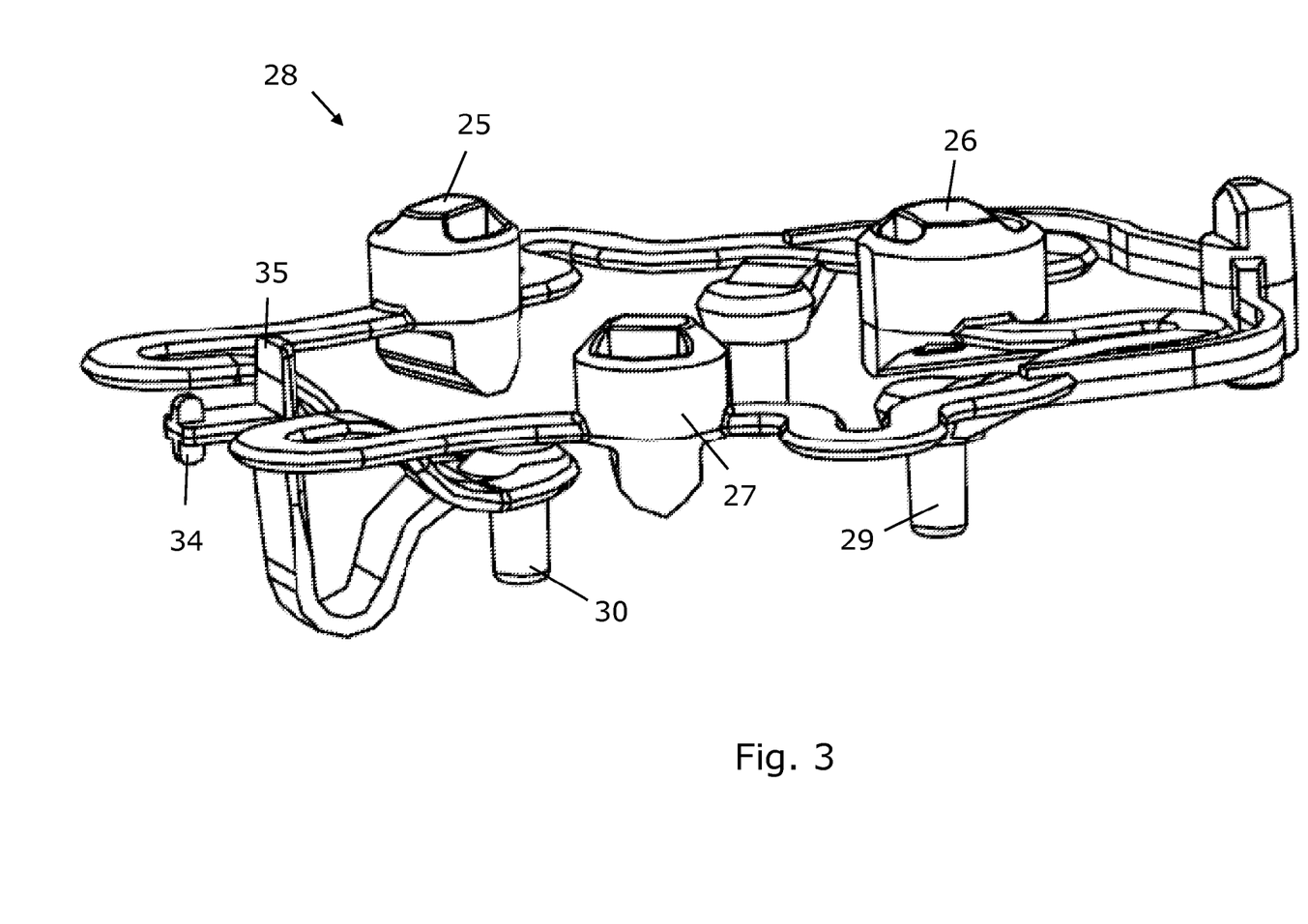
FIG. 3 illustrates an enlarged view of pinching elements from FIG. 2.
Figure 6:
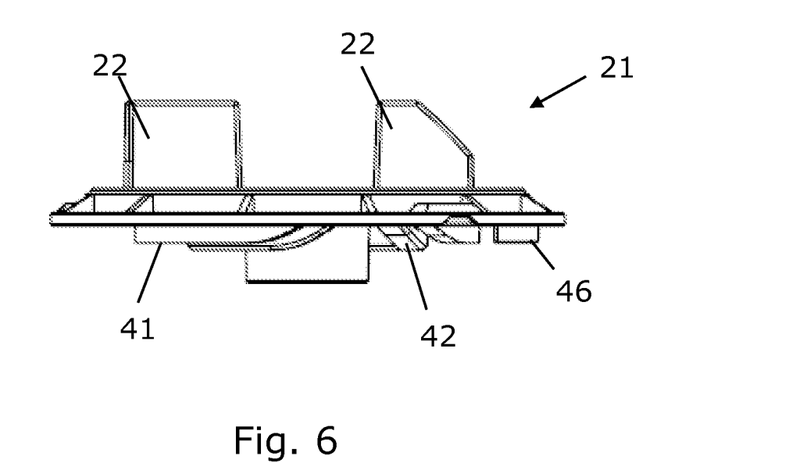
FIGS. 6, 7 illustrate a plate-shaped element forming part of the selection handle.

The conduits are made from a soft and deformable silicone material. The grippable portion 3 and the plate-shaped element 21 which together form the selection handle are joined by friction via engaging protrusions 22 provided on an upper surface 23 of the plate-shaped element and depressions provided in the grippable portion (not shown). The plate-shaped element 21 has a lower surface 24 which is opposite the upper surface 23. On the lower surface, first and second pinch cam-surfaces are formed. These are seen in FIG. 6. The pinch cam-surfaces form a surface pattern which, during rotation of the selection handle, moves the pinch elements 25, 26 and 27, c.f. FIG. 3. The pinch elements are joined into one component 28 and the bridging portions joining the elements provide a spring effect which biases each pinch element in an upward direction away from the conduits and towards the pinch cam-surfaces. The bridging portion further comprises fixing means 29, 30, c.f. FIG. 3, which engage cavities in the lower housing shell 10 and fix the component 28 to the lower housing shell 10 by friction. A nut 31 made from metal is encapsulated in a cavity in the lower housing shell 10 and cooperates with the screw 32 to hold the plate-shaped element 21 relative to the lower housing shell 10 and to allow rotation between the plate-shaped element relative to the lower housing shell.

The device comprises a venting valve 33 which can open a passage between the balloon conduit 11 and an ambient space to deflate the balloon, and between the reservoir conduit 14 and the ambient space to depressurize the reservoir. The venting valve is a one way valve in which the movable valve member is pushed to open the valve by use of the actuation pin 34, c.f. FIG. 3, which is moved by the release pin 35, c.f. FIG. 3, via contact with a release cam-surface, e.g. in the form of a protrusion or an edge of the plate-shaped element 21.

The device further comprises a check valve 36 which allows only a one-way communication of air and thereby prevents release of air from the balloon conduit and from the reservoir conduit.

Figure 4:
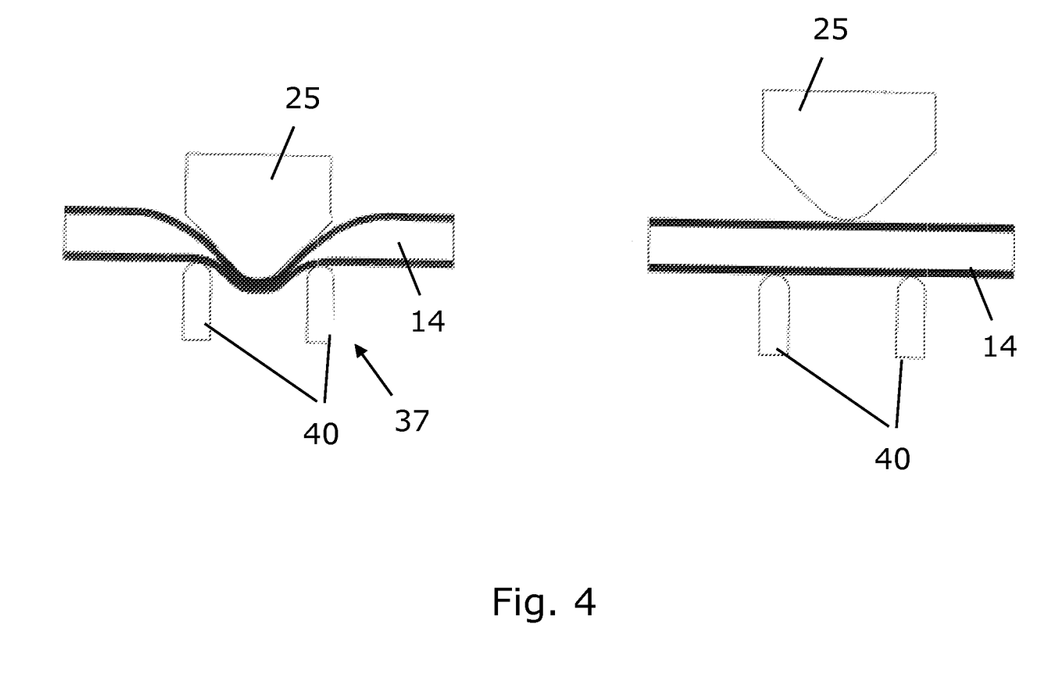
FIG. 4 illustrates a cross-section of a pinch structure including a base and a pinch element.

The device comprises a pinch structure by which the conduits are pinched between the aforementioned pinch elements 25, 26, 27 and corresponding base portions 37, 38, 39 which are fixed relative to the conduits. The pinch elements are slidingly received in cylindrical sidewalls of the base portions, c.f. FIG. 4 in which it is illustrated how the conduits are kinked between two wall portions 40 of the base portions and the pinch elements.

Figure 5:
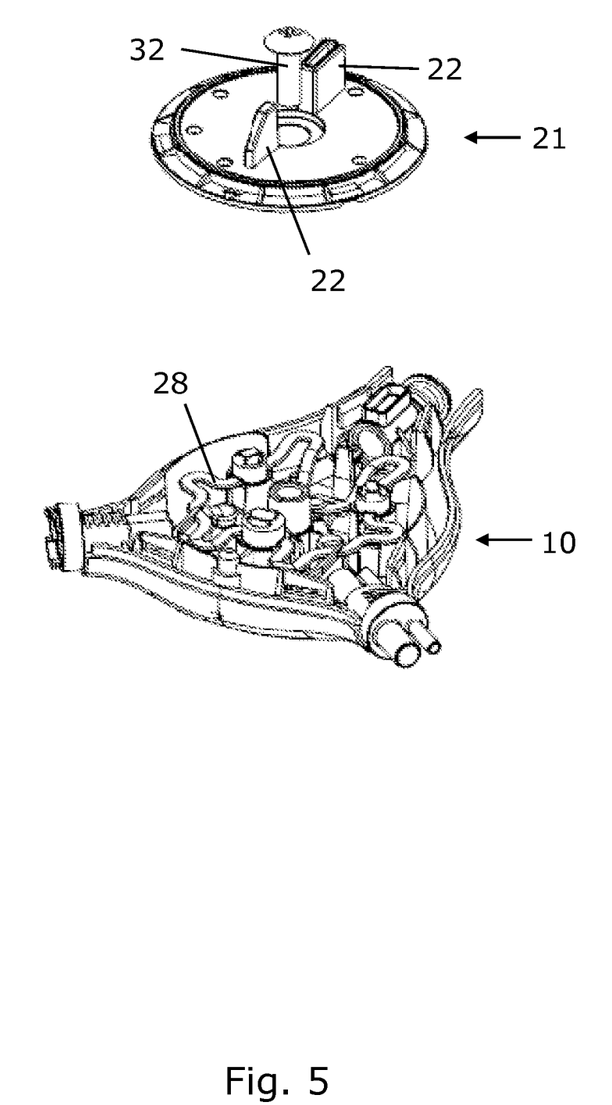
FIG. 5 illustrates the switching device in a partly assembled state.

FIG. 5 illustrates a partly assembled device where the component 28 is arranged in the lower housing shell 10 and where the plate-shaped element 21 is illustrated above the lower housing shell 10. The grippable portion of the selection handle is not shown.

Figure 7:
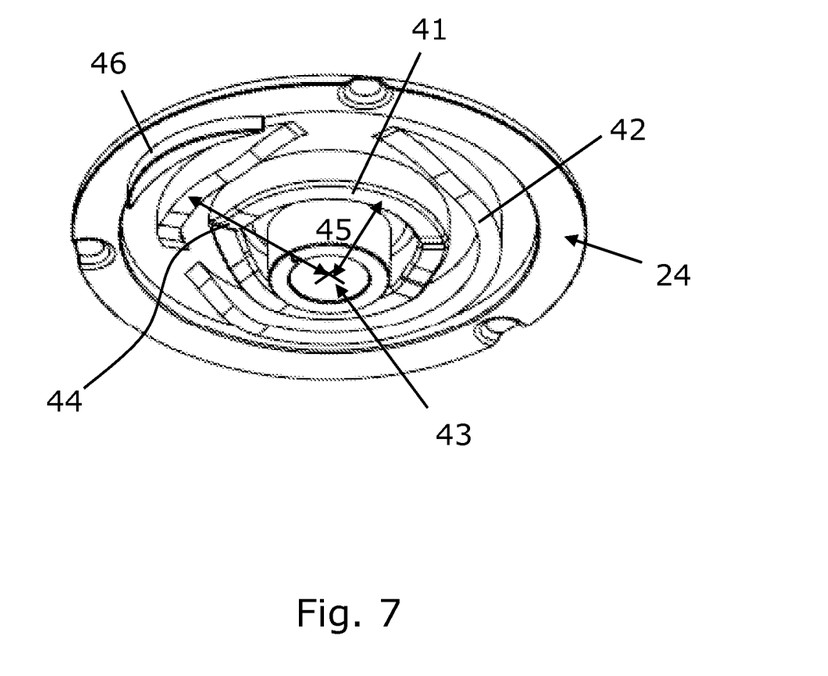

FIGS. 6 and 7 illustrate the lower surface 24 of the plate-shaped element 21. The lower surface comprises a first pinch cam-surface 41 and a second pinch cam-surface 42. Each pinch cam-surface forms a ring shaped elevation pattern which each operates one or two of the pinch elements by pressing the pinch elements towards corresponding conduits. The radial distances from the rotational center point 43 (illustrated by the arrows 44, 45) are different.

The plate-shaped element 21 further comprises a release cam surface 46 which moves the release pin 35, c.f. FIGS. 2, 3, and thus activates the release valve 33.

Figure 8:
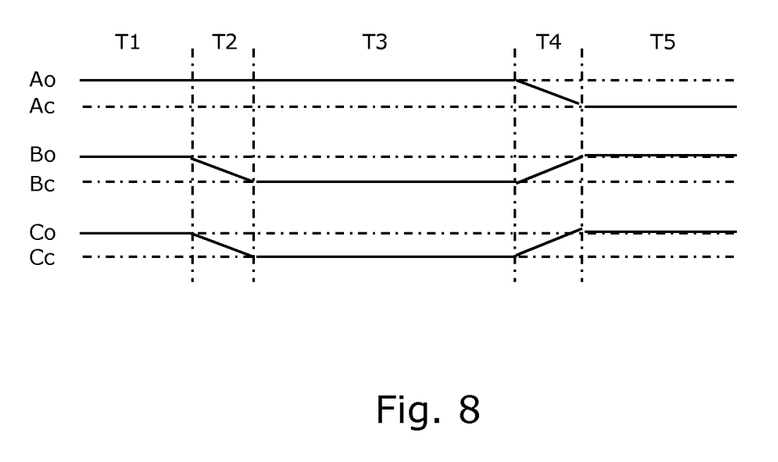
FIG. 8 illustrates an irrigation sequence in schematic form.

FIG. 8 illustrates the irrigation sequence schematically. Ao indicates the balloon conduit in an open state, Ac indicates the balloon conduit in a closed state. Bo indicates the reservoir conduit in an open state, Bc indicates the reservoir conduit in a closed state. Co indicates the delivery conduit in an open state, Cc indicates the delivery conduit in a closed state. T1-T5 indicates states in a cycle obtained by 360 degrees rotation of the selection handle.

The invention claimed is:

1. A switching device for an irrigation system, the switching device comprising a balloon conduit, a reservoir conduit, a delivery conduit, a pinching structure, and a selection handle arranged to rotate around a centre-point, the pinching structure comprising first and second pinch cam-surfaces each arranged to control deformation of at least two of the conduits in accordance with an irrigation sequence during rotational movement of the handle relative to the conduits;
wherein the pinching structure comprises base portions which are fixed relative to the conduits and pinch elements movable relative to the base portions, each base portion and corresponding pinch element arranged on opposite sides and in direct contact with the conduit to allow pinching of the conduit between a respective base portion and corresponding pinch element;
wherein each pinch element is movable to provide an outer pressure capable of deforming a conduit, the pinch cam-surface being arranged to engage and move the pinch elements during rotation of the selection handle;
wherein said first and second pinch cam-surfaces are ring-shaped and radially displaced to rotate around the centre-point at different radial distances from the centre-point, and the pinch elements are correspondingly radially displaced from the centre-point to ensure that the pinch cam-surfaces move different pinch elements during rotation of the selection handle.

2. A device according to claim 1, further comprising a release valve for opening a passage between at least one of the conduits and an ambient space, the release valve being controllable via a release cam-surface which activates the release valve during movement of the handle relative to the conduits.

3. A device according to claim 1, wherein the selection handle is arranged to rotate around a centre axis extending in an axial direction, one of the pinch cam-surfaces facing in the axial direction and the other one of the pinch cam surfaces facing radially outwardly relative to the centre axis.

4. A device according to claim 1, wherein the irrigation sequence comprises a sub-sequence in which one of the first and second pinch cam-surfaces maintains one of the conduits in one state while the other one of the first and second pinch cam-surfaces switches the state of another conduit between an open and a closed state.

5. A device according to claim 1, wherein the device is configured so that operation through the irrigation sequence includes a state in which all conduits are open.

6. A device according to claim 1, wherein each conduit is pinched between the pinch element and two wall parts of the base portion, the pinch element being arranged to press against the conduit at a location between the two wall parts.

7. A device according to claim 1, wherein the bridge portions provides a spring force on the pinch element in a direction towards one of the pinch cam-surfaces.

8. A device according to claim 1, wherein one of the first and second pinch cam-surfaces maintains one of the conduits in one state, e.g. an open, un-pinched state while the other one of the first and second pinch cam-surfaces switches the state of another conduit between an open state and a closed state.

9. A device according to claim 1, wherein the pinch elements are slidingly received in guides provided in the base portions.

10. A device according to claim 1, wherein all pinch elements are connected by bridge portions so that they form part of a single component.

* * * * *